United States Patent [19]

Braga

[11] Patent Number: 4,910,220

[45] Date of Patent: Mar. 20, 1990

[54] PHARMACEUTICAL COMPOSITIONS CONTAINING THIO-DIOXOLANE DERIVATIVES HAVING MUCOLYTIC ACTIVITY

[75] Inventor: Piercarlo Braga, Rho, Italy

[73] Assignee: Proter Spa, Italy

[21] Appl. No.: 184,057

[22] Filed: Apr. 20, 1988

[30] Foreign Application Priority Data

Apr. 22, 1987 [IT] Italy .................... 47874 A/87

[51] Int. Cl.$^4$ .................... A61K 31/335; C07D 311/20
[52] U.S. Cl. .................... 514/467; 549/453; 549/454
[58] Field of Search .................... 549/454, 453; 514/467

[56] References Cited

U.S. PATENT DOCUMENTS 4,588,824  5/1986  Baldwin et al. .................... 549/453

Primary Examiner—Nicky Chan
Attorney, Agent, or Firm—Arnold, White & Durkee

[57] ABSTRACT

The present invention relates to pharmaceutical compositions containing thiodioxolane derivatives having an interesting mucolytic activity, and to a process for the preparation of said thiodioxolane derivatives of the general structural formula

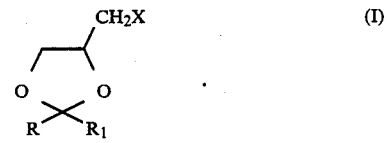

in which the carbon atom marked with an asterisk indicates a asymmetry center in the molecule, X represents an hydroxy group or —SR″ and R″ is hydrogen or a suitable acylic radical, R represents hydrogen, a lower alkyl, a lower hydroxy alkyl, or phenyl, R′ represents a lower alkyl, a lower hydroxy alkyl, phenyl, —(CH$_2$)$_n$SR″ where n is a whole number between 1 and 3 and R″ has the above indicated meaning, with condition that X and R′ can never be both type of groups.

12 Claims, No Drawings

PHARMACEUTICAL COMPOSITIONS CONTAINING THIO-DIOXOLANE DERIVATIVES HAVING MUCOLYTIC ACTIVITY

The present invention relates to pharmaceutical compositions containing thiodioxolane derivatives having an interesting mucolytic activity, use thereof and to a process for the preparation of said thiodioxolane derivatives. More particularly the compounds which are an object of the invention are of structural formula

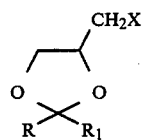

in which the carbon atom marked with an asterisk indicates an asymmetry center in the molecule, X represents an hydroxy group or —SR" and R" is hydrogen or a suitable acyl radical, R represents hydrogen, a lower alkyl, a lower hydroxy alkyl, or phenyl, R" represents a lower alkyl, a lower hydroxyl alkyl, phenyl, or —(CH$_2$)$_n$SR" where n is a whole number between 1 and 3 and R" has the above indicated meaning, with the condition that X and R' can never both be thio groups.

The compounds of formula (I) possess an interesting mucolytic activity which makes them suitable to be administered in cases in which there is an iperproduction of bronchial mucus.

The compounds of formula (I) are prepared starting from the corresponding hydroxydioxolan compounds by introduction of a thiogroup. In case the starting molecule contains more than one hydroxy group, they can be suitably protected with groups which can be easily removed.

More particularly, the compounds of formula (I) in which the thiogroup is present substituted at the carbon atom in position 4 (X=SR') are prepared after previous preparation of the corresponding mesylate, reacting first at low temperature, in an anhydrous suitable organic solvent, the 4-hydroxy-dioxolane derivative (III) with methane sulphonyl chloride and then treating the mesylate (II) in a suitable polar solvent, at a temperature between 25° and 80° C., with a suitable alkaline thioacylate, to obtain the corresponding thioester (Ia) from which, if desired by alkaline hydrolysis and successive acidification, the thioderivative (Ib) is obtained.

The process may be represented as follows

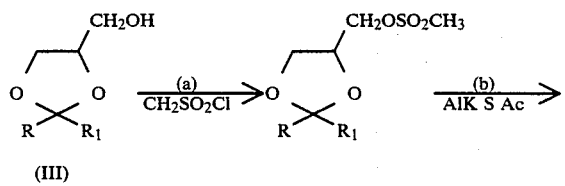

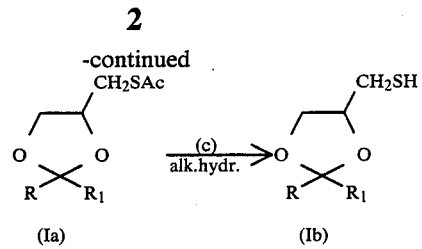

where R has the mentioned meaning; R$_1$ is lower alkyl, lower hydroxyalkyl, or phenyl; Alk is an alkaline metal, Ac is a suitable, easily removable acyl radical.

The dioxolane 4-hydroxy derivative (III) may be obtained by reaction of glycerol with a suitable carbonyl compound RCOR$_1$ in which R and R$_1$ have the mentioned meanings.

The formation of the dioxolane 4-hydroxy derivative (III) takes place in the presence of an acidic catalyst such as sulfuric acid, p-toluensulfuric or trichloro-acetic acid, in a solvent such as benzene or toluene, which allow the continuous elimination of the formed water. As an alternative, to remove the water, one can use molecular sieves.

The compounds of formula (I) in which the thio group is present substituted at the carbon atom in position 2(R'=(CH$_2$)$_n$SR") are, preferably, prepared starting from the 2-Iodo alkyl derivative (IIc), which is reacted, as described above, directly with an alkaline thioacylate formula AlkSAc (reaction b) to give the thioester (Ic) which, eventually, by alkaline hydrolysis (reaction c) gives the thiol derivative (Id).

Schematically:

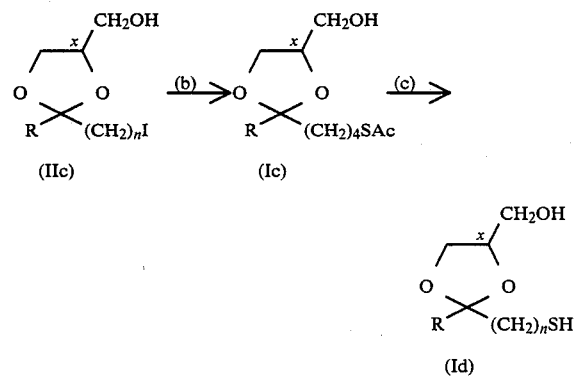

where R, Alk and Ac have the mentioned meanings.

The compounds of formula (I), in dependence on the configuration assumed by the substituent bound to the carbon atom present in position 4 of the dioxolane ring, may be in dextro or levo form; the enanthiomer may be obtained by resolution of the corresponding racemic compound, following known techniques or starting from optically active compounds.

The compounds of the invention were tested in vitro on human mucus; the results of the rheological study prove their validity as particularly active anti-cough agents. The rheological study on the mucus was made by means of a "dynamic test", using the synousoidal oscillation technique. Applying this technique we have use a rotational rheometer (LS 30S) having concentric and coaxial cylinders (Couttetype), suitably equipped.

0.1 milliliters of bronchial mucus, obtained from bronchopneumatic patients in steady state conditions, was placed in the rheometer cylindrical container, and then the second cylinder which is suspended by suitably calibrated tortion wire, was placed therein and functioned as an indicator of the viscosity and elasticity variations of the sample under examination. The mucus sample was put under stress with a synousoidal oscillating movement of 0.3 sec$^{-1}$ and the resulting answers were registered as Lissajous figures in ellipsoidal form on a plotter XY. The mathematical solution of the equations relating to the in phase components and to the ones with a phase delay, graphically represented in the ellipse, provided a quantitative measure of the degree of viscosity and elasticity of the mucus sample under investigation. This measurement was carried out on the same sample, first under basal conditions and then after adding 0.1 ml of the substance under examination and incubation at 36° C. for 10 minutes. The results are reported in the following table

| Compound | Before | | After | |
|---|---|---|---|---|
| | Viscosity (mPa · s) | Elasticity (mPa · s) | Viscosity (mPa · s) | Elasticity (mPa · s) |
| Solution | 8.011,09 | 43,30 | 7.633,58 | 51,26 |
| Example 1 | 6.680,10 | 38,29 | 3.768,30 | 18,00 |
| Example 2 | 8.825,30 | 36,20 | 484,50 | 52,30 |
| Example 3 | 6.950,60 | 54,15 | 7.600,10 | 27,10 |

The examples that follow will illustrate the invention without limiting it.

EXAMPLE 1

2-(acetyl thio)ethyl-1,3-dioxolane-4-methanol 25.8 g of 1,3-dioxolan-2-iodoethyl-4-methanol in 100 ml dimethyl formamide are treated with 20 g potassium thioacetate and the solution is left standing at room temperature for 2 hours. At the end of the reaction, the mixture is poured into 500 ml water and extracted 3 times with ethyl acetate. The solution is then washed with water followed by distillation under normal pressure first of the solvent and then of 19 g of 2-(acetylthio)ethyl-1,3-dioxolane-4-methanol. Yield 92%.

Elementary analysis for $C_8H_{14}O_4S$: calculated: C 46.6%; h 6.8%. found: C 46.8%, 7.0%.

EXAMPLE 2

1,3-dioxolane-2-ethylthio-4-methanol

A solution containing 21 g of 2-(acethylthio)ethyl-1,3-dioxolane-4-methanol, prepared as described above, in 30 ml ethyl alcohol, is treated with an equivalent amount of a 1M sodium hydroxide solution, for 8 hours at room temperature. The solution is concentrated by distillation under reduced pressure, acidified to pH 5, extracted 3 times with 50 ml ethyl ether, then washed with a saturated solution of sodium bicarbonate. The ethyl ether is distilled off and then, by distillation at 130°-136° (12 mm Hg), 12 g of 1,3-dioxolane-2-ethylthio-4-methanol are obtained. Yield 82%.

Elementary analysis for $C_6H_{12}O_2S$: calculated: C 48.65%; H 8.1%. found: C 48.8%; H 8.3%.

EXAMPLE 3

2,3-Isopropylidene-1-acetylthioglycerol 90 g glycerol & 100 ml acetone are heated under reflux for 12 hours in the presence of 5 g p-toluene sulphonic acid and 100 g molecular sieves. At the end of the reaction the solid residue is filtered out, acetone is removed by distillation under reduced pressure and 50 ml of a saturated sodium bicarbonate solution are added. The reaction mixture is extracted 3 times with 100 ml each time of ethyl acetate and the organic extract is washed with water and dried on sodium sulphate. Ethyl acetate is then removed by distillation under normal pressure and, by distillation at 74°-78° C. (12 mm Hg), 116 g of 2,3-isopropylidene glycerol are obtained. Yield 88%.

Elementary analysis for $C_6H_{12}O_3$: calculated: C 54.5%; H 9.1%. found: C 54.8%; H 9.2%.

66 g of 2,3-isopropylidene glycerol are treated at −5° C. with 51 g triethylamine and 57 g of methane sulphonyl chloride in 200 ml anhydrous methylene chloride. After 3 hours the ammonium salts which have formed are removed by filtration and the organic solution is concentrated to dryness under reduced pressure. The solid residue is dissolved in 100 ml dimethylformamide and is treated with 60 g potassium thioacetate at 80° C. for 9 hours. The reaction mixture is then poured in 500 ml water, extracted 3 times with 100 ml each time ethylacetate, and the extract is washed with water. The ethylacetate and then 82 g of 2,3-isopropylidene-1-acetyl thioglycerol are distilled under normal pressure. Yield 87%.

Elementary analysis for $C_8H_{14}O_3S$: calculated: C 50.5%; H 7.4%. found: C 50.8%; H 7.6%.

EXAMPLE 4

2,3-Isopropylidene-1-thioglycerol

A solution containing 74 g 2,3-isopropyliden-1-acetyl thioglycerol in 50 ml ethyl alcohol are treated with 80 ml of a 5M sodium hydroxide solution for 5 hours at room temperature. The solution is then concentrated by distillation under reduced pressure, acidified to pH 5, extracted 3 times with 50 ml each time of diethyl ether, and the extract is washed with a saturated solution of sodium bicarbonate. After removing the ether by distillation under normal pressure, 62 g of 2,3-Isopropylidene-1-thioglycerol are distilled at 90°-96° C. (12 mm Hg). Yield 84%.

Elementary analysis for $C_6H_{12}O_2S$: calculated: C 48.65%; H 8.1%. found: C 48.8%; H 8.3%.

EXAMPLE 5

1,3-dioxolane-2-methyl-2'-phenyl-4-acetylthiomethylene 90 g glycerol and 150 ml acetophenone are heated under reflux for 12 hours in the presence of 5 g p-toluensulphonic acid and 100 g molecular sieves; the solid residue is filtered, a saturated solution of sodium bicarbonate is heated and the mixture is extracted 3 times with 100 ml ethyl acetate. The organic extract is then washed with water, dried on sodium sulphate and ethyl acetate is removed by distillation. The obtained product is distilled at 122°-126° C. (1 mm Hg) and gives 140 g of pure 1,3-dioxolane-2-methyl-2'-phenyl-4-methanol. Yield 72%.

Elementary analysis for $C_{11}H_{14}O_3$: Calculated: C 68.05%; H 7.2%. Found: C 68.3%; H 7.4%.

19.4 g 1,3-dioxolane-2-methyl-2'-phenyl-4-methanol are treated at −5° C. in 100 ml anhydrous methylene chloride with 10 g triethylamine and 11.4 g methanesulfonylchloride. After 3 hours the reaction mixture is filtered and the organic solution is distilled to dryness under reduced pressure. The residue is dissolved in 25 ml of methylformamide and treated with 12 g potassium thioacetate at 78° C. for 9 hours. At the end of the reaction the mixture is poured in 100 ml water, extracted 3 times with 25 ml each time of ethyl acetate and the organic solution is then washed with water.

The ethylacetate is distilled under normal pressure and then at 98°–102° C. 16.4 g 1,3-dioxolane-2-methyl-2′-phenyl-4-acetyl-thiomethylene are obtained.

Elementary analysis for $C_{13}H_{16}O_3S$: Calculated: C 61.9%; H 63.5%. Found: C 62.2%; H 62.5%.

EXAMPLE 6

2,3-dioxolane-2-methyl-2′-phenyl methanethiol

A solution containing 25 g 1,3-dioxolane-2-methyl-2′-phenyl-4-acetylthiomethylene in 20 ml ethyl alcohol is treated with an equivalent amount of 1M sodium hydroxide solution for 5 hours at room temperature. The solution is then concentrated by distillation under reduced pressure and acidified to pH 5. It is then extracted 3 times with 50 ml ethyl ether each time, the extract is washed with a saturated solution of sodium bicarbonate, the ether is removed by distillation under normal pressure, and by distillation at 125°–130° C. (12 mm Hg) 17.1 g 1,3-dioxolane-2-methyl-2′phenyl-4-methanethiol are obtained. Yield 82%.

Elementary analysis for $C_{11}H_{14}O_2S$: Calculated: C 62.85%; H 6.79%. Found: C 62.0%; H 6.85%.

EXAMPLE 7

1,3-dioxolane-2-methyl-2′-(2-hydroxyethyl)-4-acetylthiomethylene

The method described in Example 5 is followed starting with glycerol and 4-hydroxy-2-butanone, suitably protected at the hydroxy group with an acetyl radical. 4-acetoxy-2-butanone is prepared starting from ethyl acetoacetate, protected at the carbonyl group as diethylacetal, by reduction with lithium-aluminium hydride, followed by restoring the keto group by means of silica in the presence of water (A: Banerje 8 G. P. Kalena, Synth. Commun (1982) 12, 225). 1,3-dioxolane-2-methyl-2′-(2-hydroxyethyl-4-acetylthiomethylene distills at 164°–170° C. (10 mm Hg). Yield 61%.

Elementary analysis for $C_{11}H_{18}O_5S$: Calculated: C 50.4%; H 6.9%. Found: C 50.6%; H 7.0%.

EXAMPLE 8

1,3-dioxolane-2-methyl-2′-(2-hydroxyethyl)-4-methanthiol

The method described in Example 6 is followed starting from 1,3-dioxolane-2-methyl-2′(2-hydroxyethyl)4-acetyl-thiomethylene. 1,3-dioxolane-2-methyl-2′-(2-hydroxyethyl)4-acetyl-thiomethylene. 1,3-dioxolane-2-methyl-2′-(2-hydroxyethyl)4-methanethiol distills at 132°–134° C. (10 mm Hg). Yield 85%.

Elemental analysis for $C_7H_{14}O_3S$: Calculated: C 47.2%; H 7.9%. Found: C 47.4%; H 8.0%.

EXAMPLES 9 & 10

(S)-(+)-2,3-isopropyliden-acetylthio-glycerol
(S)-(+)-2,3-isopropyliden-1-thioglycerol A mixture containing 5 g zinc chloride in 30 ml anhydrons acetone and 2 g molecular sieves (3 Å) is prepared and left under stirring for three days.

The sieves are removed by filtration and the reaction mixture is poured in a solution of 6.8 g potassium carbonate in 7 ml distilled water and 20 ml ethyl ether. A white precipitate forms which is filtered and washed with several portions of a 1:1 ether:acetone mixture. The solution is evaporated under reduced pressure and 3 g of S-(+)-1,2-isopropylideneglycerol are obtained, which are dissolved in 100 ml methyl alcohol and treated with a solution of potassium periodate in 25 ml water and 100 mg lithium hydroxide. After 15 minutes, 25 ml methyl alcohol are added and a 5N potassium hydroxide solution to pH 8. After cooling to −10° C., the mixture is filtered on a paper filter and 400 mg sodium borohydride are added to the filtrate; after standing for 1 hour at room temperature, the mixture is extracted three times with 20 ml chloroform. After drying on sodium sulphate, the solvent is evaporated, and 2 g (S)-(+)-1,2-isopropylideneglycerol are obtained. B.p: 33° C. (0.1 torr); $\alpha_D = +15.6°$ (pure liquid).

Following the previously described method (Example 3) of formation of the corresponding mesylate, successive obtainment of (S)-(+)-2,3-isopropylidene-1-acetylthio-glycerol (85% yield) and then, through hydrolysis (Example 4), formation of (S)-(+)-2,3-isopropylidene-1-thioglycerol, which distills at 90°–96° C. (12 mm Hg); $\alpha_D = +8°$ C. =3; ethyl alcohol).

Elementary analysis for $C_6H_{12}O_2S$: calculated: C 48.65%; H 8.1%. Found: C 48.8%; H 8.3%.

In a similar way (R)-(−)2,3-isopropylidene-1-acetyl-thioglycerol and then (R)-(−)-2,3-isopropylidene-1-thioglycerol are prepared, starting from (R)-(−)-1,2-isopropylideneglycerol which is obtained from ascorbic acid by the method described by C. Hubschwerlen (Synthesis, 1986, 942).

The pharmaceutical compositions according to the present invention may be administered by the oral route, by intramuscular injection or as suppositories, admixed with usual diluents.

The active ingredient selected among the compounds of formula (I) must be present in an amount comprised between 1 and 10 mg/kg. We give hereinafter some specific examples of pharmaceutical formulations

| 1. Tablets | | |
|---|---|---|
| microcrystalline cellulose | mg | 35 |
| carboxymethylstarch | mg | 10 |
| Na carboxymethylcellulose | mg | 5 |
| Colloidal $SiO_2$ | mg | 4 |
| povidon | mg | 8 |
| compound of Ex. 1 | mg | 300 |
| magnesium stearate | mg | 20 |
| dibasic calcium phosphate | mg | 120 |
| opadry-y-1-7000 | mg | 10 |
| granulates | | |
| compound of Ex. 2 | mg | 200 |
| saccharin | mg | 8 |
| orange flavor | mg | 87 |
| dry orange juice | mg | 4,8 |
| saccharose | g | 4.225 |
| granulates | | |
| compound of Ex. 3 | mg | 100 |
| saccharin | mg | 8 |
| orange flavor | mg | 20 |
| orange lyophilized | mg | 500 |
| saccharose | g | 4.37 |
| Suppositories for adult | | |
| compound of Ex. 1 | mg | 200 |
| triglycerides | g | 2.8 |
| Suppositories for child | | |
| compound of Ex. 1 | mg | 100 |
| triglycerides | g | 1.0 |
| Suppositories for breast-fed | | |
| compound of Ex. 1 | mg | 50 |
| triglycerides | g | 0.85 |
| Vial for i.m. injection | | |
| compound of Ex. 3 | mg | 200 |
| distilled water | ml | 3 |

-continued

1. Tablets

The same vial may be used for aerosol.
Glass of 10 ml as oral syrup

| compound of Ex. 1 | mg | 200 |
| sorbitol | g | 1.5 |
| ethyl alcohol | ml | 0.1 |
| methyl p.hydroxy benzoate | g | 0.01 |
| saccharose | g | 4.8 |
| orange flavor 1% | ml | 0.016 |
| pineapple flavor 1% | ml | 0.016 |
| distilled water | ml | 5.54 |

I claim:

1. A pharmaceutical composition having mucolytic activity which comprises a therapeutically effective amount of one or more compounds of the general formula

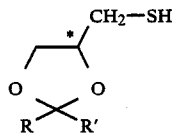

where the carbon atom marked with an asterisk indicates an asymmetry center in the molecule,
R represents hydrogen, a lower alkyl, a lower hydroxyalkyl, a phenyl,
R' represent a lower alkyl, a lower hydroxy-alkyl, or phenyl, in admixture with one or more pharmaceutically acceptable carriers.

2. The pharmaceutical composition of claim 1 wherein the said compound is: 1,3-dioxolane-2-ethyl-4-thiomethanol.

3. The pharmaceutical composition of claim 1 wherein the said compound is 2,3-isopropylidene-1-thio-glycerol.

4. The pharmaceutical composition according to claim 1 wherein the said compound is (S)-(+)-2,3-isopropylidene-1-thioglycerol.

5. A therapeutic method for the treatment of iperproduction of bronchial mucus by administering orally or parenterally a pharmaceutical composition of claim 1.

6. The therapeutic method according to claim 5 by administering a pharmaceutical composition wherein the compound is 1,3-dioxolane-2-ethyl-4-thiomethanol.

7. A therapeutic method of claim 5 by administering a pharmaceutical composition wherein the compound is 2,3-isopropylidene-1-thio-glycerol.

8. The therapeutic method of claim 5 by administering a pharmaceutical composition wherein the compound is (S)-(+)-2,3-isopropylidene-1-thio-glycerol.

9. A compound having the general formula:

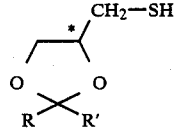

wherein the carbon atom marked with an asterisk indicates an asymmetry center in the molecule, R represents hydrogen, lower alkyl, lower hydroxyalkyl, or phenyl, and R' represents lower alkyl, lower hydroxyalkyl, or phenyl.

10. The compound of claim 9 wherein the said compound is 2-ethyl-1,3-dioxolane-4-thiomethanol.

11. The compound of claim 9 wherein R=R'=CH$_3$.

12. The compound of claim 11 which is (S)-(+)-2,3-isopropylidene-1-thio-glycerol.

* * * * *